US011406235B2

(12) United States Patent
Möwisch (10) Patent No.: US 11,406,235 B2
(45) Date of Patent: Aug. 9, 2022

(54) AUTONOMOUS DOMESTIC APPLIANCE AND SEATING OR RECLINING FURNITURE AS WELL AS DOMESTIC APPLIANCE

(71) Applicant: SERVICE-KONZEPTE MM AG, Hannover (DE)

(72) Inventor: Anja Möwisch, Hannover (DE)

(73) Assignee: SERVICE-KONZEPTE MM AG, Hannover (DE)

(*) Notice: Subject to any disclaimer, the term of this patent is extended or adjusted under 35 U.S.C. 154(b) by 643 days.

(21) Appl. No.: 16/472,667

(22) PCT Filed: Nov. 23, 2017

(86) PCT No.: PCT/EP2017/080231
§ 371 (c)(1),
(2) Date: Jun. 21, 2019

(87) PCT Pub. No.: WO2018/114209
PCT Pub. Date: Jun. 28, 2018

(65) Prior Publication Data
US 2019/0365170 A1    Dec. 5, 2019

(30) Foreign Application Priority Data

Dec. 21, 2016  (DE) .................... 10 2016 125 199.2
Mar. 8, 2017   (DE) .................... 10 2017 104 846.4

(51) Int. Cl.
*A47L 9/00*     (2006.01)
*A47C 7/72*     (2006.01)
(Continued)

(52) U.S. Cl.
CPC .............. *A47L 9/009* (2013.01); *A47C 7/72* (2013.01); *A47C 7/723* (2018.08); *A47C 7/727* (2018.08);
(Continued)

(58) Field of Classification Search
None
See application file for complete search history.

(56) References Cited

U.S. PATENT DOCUMENTS 5,553,609 A   9/1996   Chen et al.
5,802,494 A   9/1998   Kuno
(Continued)

FOREIGN PATENT DOCUMENTS

CN   106037326 A    10/2016
DE   195 17 037 A1  11/1996
(Continued)

OTHER PUBLICATIONS

IBM, "Computer-in-an-Armchair," Technical Disclosure Bulletin, vol. 32, No. 9B, Feb. 1990.

*Primary Examiner* — Bhavesh V Amin
(74) *Attorney, Agent, or Firm* — WCF IP (57) ABSTRACT

The invention relates to an autonomous domestic appliance (1) in the form of a floor cleaning robot or a lawn mower robot with a platform (3) which comprises means of locomotion (4), environmental sensors (5a, 5b, 5c) for detecting properties of the environment of the autonomous domestic appliance (1) and a control unit (6). The environmental sensors (5a, 5b, 5c) are connected to the control unit (6), and the control unit (6) is designed for autonomous movement of the domestic appliance (1) by actuating the means of locomotion (4) as a function of the detected environmental properties and for permanent travel in an area for carrying out its actual domestic activity. The autonomous domestic appliance (1) has a communication unit (7) for establishing a communication link with a remotely arranged service unit (2) and, in addition to its actual domestic activity, is designed to detect the need of help of a person as a function of the environmental properties.

19 Claims, 5 Drawing Sheets

(51) Int. Cl.
*A47L 11/40* (2006.01)
*A47C 7/70* (2006.01)
*A61B 5/11* (2006.01)

(52) U.S. Cl.
CPC ............ *A47L 11/4011* (2013.01); *A47C 7/70* (2013.01); *A47L 2201/04* (2013.01); *A61B 5/1126* (2013.01)

(56) References Cited

U.S. PATENT DOCUMENTS

| | | | |
|---|---|---|---|
| 6,002,994 A | 12/1999 | Lane et al. | |
| 7,228,203 B2* | 6/2007 | Koselka | B25J 19/023 700/246 |
| 8,509,947 B2* | 8/2013 | Jarisch | A47J 31/407 221/96 |
| 8,786,429 B2* | 7/2014 | Li | G05D 1/0033 205/687 |
| 9,747,772 B2* | 8/2017 | Feiten | G16H 40/67 |
| 10,730,397 B2* | 8/2020 | Romanov | A47L 11/4061 |
| 10,766,132 B2* | 9/2020 | Romanov | G05D 1/0219 |
| 2005/0154265 A1* | 7/2005 | Miro | G07C 9/37 704/E15.045 |
| 2005/0216126 A1* | 9/2005 | Koselka | B25J 5/007 700/259 |
| 2006/0176182 A1 | 8/2006 | Noguchi et al. | |
| 2007/0198129 A1* | 8/2007 | Koselka | G05D 1/0251 700/245 |
| 2009/0319079 A1* | 12/2009 | Arceta | A61G 12/001 700/228 |
| 2013/0100268 A1 | 4/2013 | Mihailidis et al. | |
| 2013/0245827 A1 | 9/2013 | Shetty | |
| 2014/0091604 A1 | 4/2014 | Chatrenet et al. | |
| 2014/0313029 A1* | 10/2014 | Feiten | G16H 40/67 340/539.12 |
| 2015/0094914 A1* | 4/2015 | Abreu | B60H 1/00742 701/1 |
| 2015/0223705 A1 | 8/2015 | Sadhu | |
| 2015/0273697 A1 | 10/2015 | Abdullah | |
| 2016/0058245 A1 | 3/2016 | Smith et al. | |
| 2016/0085935 A1* | 3/2016 | Waterson | G16H 50/20 705/2 |
| 2016/0266577 A1 | 9/2016 | Kerzner | |
| 2019/0365170 A1* | 12/2019 | Möwisch | B01F 33/846 |
| 2020/0069134 A1* | 3/2020 | Ebrahimi Afrouzi | G05D 1/0248 |

FOREIGN PATENT DOCUMENTS

| | | |
|---|---|---|
| DE | 196 14 916 A1 | 11/1997 |
| DE | 20 2006 004 282 U1 | 6/2006 |
| DE | 20 2012 000 410 U1 | 4/2012 |
| DE | 10 2011 053 990 A1 | 3/2013 |
| DE | 10 2011 087 589 A1 | 5/2013 |
| DE | 10 2015 100 224 A1 | 7/2016 |
| EP | 0 753 160 B1 | 4/2001 |
| EP | 1 566 782 A1 | 8/2005 |
| EP | 2 407 074 A2 | 1/2012 |
| EP | 2 933 953 A1 | 10/2015 |
| WO | 2008/057618 A2 | 3/2007 |
| WO | 2008/047078 A1 | 4/2008 |
| WO | 2008/059432 A1 | 5/2008 |
| WO | 2009/058839 A1 | 5/2009 |
| WO | 2013/130576 A1 | 9/2013 |
| WO | 2013/150070 A1 | 10/2013 |
| WO | 2016/180796 A2 | 11/2016 |

\* cited by examiner

AUTONOMOUS DOMESTIC APPLIANCE AND SEATING OR RECLINING FURNITURE AS WELL AS DOMESTIC APPLIANCE

The invention relates to an autonomous domestic appliance in the form of a floor cleaning robot or lawn mowing robot with a platform having means of locomotion, environmental sensors for detecting properties of the environment of the autonomous domestic appliance and a control unit, wherein the environmental sensors are connected to the control unit and the control unit is arranged for autonomous locomotion of the domestic appliance by driving the means of locomotion in dependence on the detected environmental properties and for continuously driving an area to carry out its actual domestic activity.

The invention also concerns a piece of seating or reclining furniture with a pivoting, sliding and/or telescopic service unit arranged on the piece of seating or reclining furniture.

Such autonomous household appliances are well known as suction robots for floor cleaning in buildings or mowing robots for autonomous mowing of lawns. They are equipped with suitable sensors, such as tactile sensors, inductive boundary line sensors, ultrasonic sensors, optical sensors or locating sensors, in such a way that they detect and avoid obstacles, including steps and depressions, and have worked a continuous surface at least once over a longer period of time.

The invention also concerns a household appliance for the preparation of food with a receptacle. Such household appliances are known in the form of kitchen automats, cooking automats, water boilers, tea automats, coffee automats, water jets or the like.

DE 10 2011 053 990 A1 describes, for example, an electric kitchen machine in which recipes are stored for recall.

In patient care, there is a need to ensure and monitor the medically prescribed entry of medication in the daily routine. For this purpose, DE 20 2006 004 282 U1 describes a drug dispenser for the allocation of drugs which has an unlocking mechanism triggered by the function switch for drug dispensing.

DE 20 2012 000 410 U1 describes a system for geriatric emergency and vital parameter communication to control the medication intake of a patient, which is designed as a portable device.

DE 10 2015 100 224 A1 reveals an implantable drug delivery system that must be surgically inserted into a cavity of the body.

US 2016/0058245 A1 shows a device that is intended exclusively for the preparation of energy drinks with food supplements, but not for administering medication.

EP 0 753 160 B1 describes a method and a device for obstacle detection for such an autonomous device. At least one microphone is provided to detect obstacles with acoustic methods.

Mobile emergency and help call systems installed in the building or to be worn on the body by the person to be cared for are also known for monitoring persons in need of help. This is intended to enable people who are restricted, for example, due to cardiovascular disorders, spasticity, tremor and dementia, to live an independent life in their own home. Such an emergency system is described for example in DE 195 17 037 A1.

US 2015/0273697 A1 and US 2005/0216126 A1 reveal autonomous service robots which are specially designed to support persons to be cared for and have a very robust platform for this purpose.

US 2005/0154265 A1 describes a robot that serves as an interface between a physician or nurse and a patient to record and transmit wishes using speech recognition.

U.S. Pat. No. 5,553,609 A describes a patient monitoring system with video cameras, microphones and speakers connected to a monitoring center.

U.S. Pat. No. 5,802,494 A reveals a corresponding patient monitor system that additionally includes specialized care robots for patient support.

US 2006/0176182 A1 shows a dog-like robot with a camera, which is specially designed to monitor the health and safety of people.

US 2016/0166577 A1 describes flying drones for surveillance.

US 2013/0245827 A1 reveals a remote monitoring system with a mobile monitoring device that monitors an area within a specified spatial zone and issues an alarm if, for example, an infant crosses this zone. In monitoring mode, the device positions itself within the range of the preset limit.

DE 10 2011 087 589 A1 describes a modular assistance system for a person that has at least one mobile unit that can be optionally equipped with exchangeable function modules for supplying the person, with measuring modules, with a cleaning module that can be remotely controlled by the person, etc. The system can also be equipped with a remote control unit.

One problem with portable emergency and auxiliary facilities, which have to be carried by the person to be looked after like a wristwatch, for example, is their acceptance. In order to ensure functionality, the care staff must ensure that he or she carries the emergency call unit with him or her. The permanent installation of emergency call systems in buildings is complex and also requires acceptance.

On the basis of this, it is therefore the task of the present invention to create a reliable and as simple as possible and hardly perceptible aid device for needy persons.

The task is solved with the autonomous household appliance with the characteristics of claim 1 and the seating or reclining furniture according to claim 11 for this purpose. Advantageous design forms are described in the subclaims.

It is proposed to use a generic autonomous household appliance as a platform complementary to the actual household activity to detect the need for assistance of a person depending on environmental characteristics, which can be detected by environmental sensors of the autonomous household appliance. The autonomous household appliance then has a communication unit set up to establish a communication link with a remote service unit. The communication unit can be set up for wireless radio communication with a radio transmitter unit or a transceiver. As an option or in addition to wireless communication, the communication unit can also be set up for wired data exchange with the service unit, e.g. by the autonomous household appliance coming into contact with a docking station in order to enable the data temporarily stored in the autonomous household appliance to be read out. The docking station may preferably be a charging station for the autonomous household appliance. This ensures that data exchange is protected against eavesdropping and manipulation. In wireless communication, this can be ensured by encrypted and/or certified data transmission.

The household appliance is a floor cleaning robot or a mowing robot that has a floor cleaning or lawn mowing unit. Such a floor cleaning robot can be, for example, a vacuum cleaner, a surface wiping robot or a combination of these.

Such a surface wiping robot can be a floor wiping robot or even a window cleaning robot.

The autonomous household appliance constantly travels the assigned area, as is usual with suction robots or mowing robots, and monitors the need for help of a person with the help of environmental sensors in addition to the actual household activity.

A person's need for help can be identified by means of a person assistance unit which has been set up for this purpose and which is integrated into the autonomous assistance device, e.g. by modular attachment to it, and which is set up for the wireless transmission of an assistance request via the communication unit in the event of a recognised need for help. Alternatively, the remote service unit, designed as a personal assistance unit, can also detect the need for assistance by means of the environmental sensor data received wirelessly from the autonomous household appliance. The autonomous household appliance is thus involved in the detection of environmental characteristics during the recognition of the need for assistance, which is ultimately carried out by the remote service unit.

With the aid of the autonomously movable platform, the autonomous household appliance with its environmental sensors can move independently in a room area and, on request, drive to the person in need of help, e.g. if a call for help is detected, and verify and report the need for help. The spatial area, i.e. the area in which the autonomous household appliance carries out its actual household activity self-propelled, is defined by the obstacle or border detection. It is assigned by the positioning of the budget area and can be delimited by border markings.

The person assistance unit is not noticeable, so that the person to be cared for does not feel completely supervised and observed and every outsider recognizes that due to health restrictions care aids are necessary. Household appliances used before the start of the need for long-term care can continue to be used as a platform and are thus accepted. The communication unit and a unit for the detection of environmental characteristics or the combination of environmental sensor data already available in the platform for forwarding by the communication unit, possibly with a preliminary evaluation, can then be attached to the platform as an additional module. A plug-on module, an clip-on module or similar is available for this purpose.

This is achieved in particular by the seating or reclining furniture, which carries the remote service unit for easy and quick interaction with the person regularly using this piece of furniture as the main food centre. The service unit has a monitor and an input unit for this purpose and is set up for wireless communication with the autonomous household appliance. A charging station for docking and charging the autonomous household appliance with electrical energy is located in the foot area of the seating or lying furniture. Thus the seating or lying furniture (armchair, chair or nursing bed) is not only the main food centre of the person to be cared for, but also the centre for the au-autonomous household appliance used for care. Due to the arrangement of the charging station in the foot area of this piece of furniture, it is not very conspicuously positioned for the person and visitor to be looked after and can be parked ready for operation in a room area where the signs of need for help that are to be detected are most likely to occur. The paths to environmental detection with the aid of environmental sensors are thus optimally shortened.

The charging station can also be designed as a docking station for establishing a wired data connection with the communication unit of the autonomous household appliance. For this purpose, the charging station and the autonomous household appliance have electrical contacts which come into contact when the autonomous household appliance is connected to the charging station. Compared to wireless communication, this ensures a considerably secure data exchange.

The stand-alone household appliance may have a camera set up with the communication unit to transmit ambient images to the service unit. With the help of this camera, more detailed image information can be transmitted to nurses and assistants, for example, when a need for help has been identified. The camera can also be used as an environmental sensor to verify a perceived need for assistance if necessary, or to identify it by comparing patterns or images based on the captured images.

The autonomous household appliance can be designed for remote control with the aid of a remotely located service unit or from a command application networked with it. This allows remote-controlled monitoring trips to be carried out by nursing staff without having to visit and enter the home of the person to be looked after and without the person being disturbed by such a visit. In this way, the person to be cared for can also make contact with a caregiver and receive help quickly and efficiently, with the intensity of remote care and contact being controllable. This enables monitoring without the physical presence of nursing staff.

The camera can be remotely adjusted and/or focused. For this purpose, the camera can have actuators for changing the pan angle, pitch angle and/or zoom ratio. It is therefore conceivable that commands entered by a remote service unit could pan the camera when it detects a need for assistance in order to determine the situation in the vicinity of the person in need of assistance and coordinate an emergency response on this basis.

The household appliance may have at least one microphone for the detection of sound signals. The auxiliary unit may then be set up to move in a controlled manner towards the sound source and/or to detect the need for assistance by means of recorded sound signals in dependence on a comparison of recorded sound signals with predefined sound patterns. With the help of the microphone, the person to be cared for can send a call for help to the autonomous household appliance. The autonomous household appliance is then in a position to verify the need for help and, using a microphone and camera for example, to establish communication between remotely available help personnel and the person in need via the remote service unit. For acoustic communication it is advantageous to integrate at least one loudspeaker in the autonomous household appliance in order to enable a bidirectional audio communication connection between the person in need of assistance and the remote service unit.

At least one environmental sensor of the household appliance may be arranged to detect characteristics of elements which can be collected from the environment by the soil cleaning or lawn mowing unit. For example, it is possible to use gas sensors, chemical sensors or optical sensors to detect whether drugs, alcohol, blood, urine or other body excrements have been collected by the household appliance. The recognition of such characteristics is then an indication of a need for help. The detection of alcohol, for example, is a sign of the spillage of liquid medicines, which are usually prepared on the basis of alcohol, and thus an indication of the danger of taking medication contrary to regulations. The environmental sensors and the downstream detection routines are preferably designed to detect pharmaceutical agents on the basis of typical excipients or pharmaceutical excipients. This may include fillers (e.g. lactose, cellulose, starch, sucrose, paraffin, hard fat, polyethylene glycol, polyethylene oxides), solvents or humectants (e.g. water, ethanol, isopropanol), emulsifiers (e.g. Cetylstearyl alcohol, glycerol monostearate, lecithin, fatty acid esters of sorbitane, polyoxyethylene sorbitan (polysorbate), polyoxyethylene, polyoxyethylene fatty alcohol ether), solubilizers or wetting agents (e.g. polyethylene glycols, polyethylene oxides, polysorbates), buffers (e.g. sodium dihydrogen phosphate, sodium bicarbonate, calcium hydrogen phosphate, trometamol), thickeners and binding agents (e.g. starches, guarane, xanthan gum, alginate, carrageenan, pectin, traganth, polyacrylic acids, polyvinylpyrrolidone; highly dispersed silica, substituted cellulose ethers (methylcellulose, ethylcellulose, hydroxypropylcellulose, hydroxypropylmethylcellulose, carboxymethylcellulose), coating agents (e.g.e.g. sucrose, gelatine, gelatine polysuccinate, polyacrylates, ethylcellulose, methylcellulose), decomposition accelerators and disintegrants (e.g. starches, croscarmellose, sodium hydrogen carbonate in combination with citric acid), lubricants and slip agents and mould release agents (e.g. polyethylene glycols, polyethylene oxides, talcum, magnesium stearate), flow regulators (e.g. highly dispersed silica), antioxidants (e.g. butylhydroxytoluene, all-rac-α-tocopherol), preservatives (e.g. PHB ester, benzalkonium chloride, benzyl alcohol, thiomersal), sweeteners and taste correctives (e.g. B. sucrose, sorbitol, sweeteners such as saccharin sodium and cyclamate; aromas) or absorption accelerators (e.g. dimethyl sulfoxide).

Environmental sensors can, for example, be integrated in the bristles or rags of a floor cleaning unit. A floor cleaning unit is not just a unit suitable for cleaning a horizontal plane. A glass or wall cleaning function for vertical levels is also conceivable, whereby such a household appliance is useful for patient monitoring due to the possible viewing angle from above, e.g. if a nursing bed stands next to a window.

In combination with a floor cleaning unit, it is conceivable to use detection liquids with which the bristles or rags can be soaked manually or automatically. By integrating optical sensors close to the bristles or lobes, the coloration of the bristles or lobes can then be examined and the environmental properties can be determined on the basis of characteristic color values or color spectra.

Such properties can be inferred, for example, if the specified threshold values are exceeded. It is also conceivable to correlate this with other recorded properties or to identify the need for assistance if such occurrences accumulate over a period of time. It is helpful to log such events for the nursing documentation in order to be able to print it out as a nursing diary or to have an open interface so that a connection to a nursing documentation of a nursing provider is possible.

An autonomous household appliance designed as a suction robot may have a transparent collection container with a coarse filter unit connected to the floor cleaning unit and suitable for collecting medicines lying on the floor. This makes it possible to quickly determine by visual inspection whether drugs have collected in the collection container which indicate that they have not been taken properly and are therefore in need of help.

The Personal Assistance Unit can be set up to activate an assistance unit that includes at least a camera and a microphone. Activation takes place when a need for assistance has been detected by means of at least one tactile sensor, gas sensor, light sensor and/or sound level sensor. Predefined threshold values, for example, can also be used here as criteria for activation. For example, a tactile sensor can be used to determine whether a person is lying on the ground. With the help of gas sensors, conspicuous compositions of the ambient air, such as a lack of oxygen or an increased urine content, can be detected. A reduced lack of oxygen in the ambient air shows that the person to be cared for is no longer able to provide regular ventilation automatically. An increased urine concentration in the air is a sign that, for example, incontinence is present or that diapers need to be changed.

The personal assistance unit can be equipped with at least one interface for connecting personal vital data sensors and for evaluating and/or transmitting sensor data collected with the personal vital data sensors via the communication unit to a remote service unit. This has the advantage that the person support unit coupled with the autonomous household appliance can still be connected wirelessly to additional devices, preferably, with the personal vital data being recorded. These can be, for example, passenger cars or, for example, pulse and heart rate monitors to be worn on the wrist or chest circumference, blood glucose monitors, body temperature monitors and the like. Data transmission is preferably wireless via suitable radio communication interfaces. These personal vital signs sensors can also be used to correlate with the environmental characteristics captured by the environmental sensors of the autonomous household appliance. This can improve the quality of the identification of the need for assistance.

Depending on the time of day or the behaviour patterns of the person to be cared for, the service unit of the seating or lying furniture can be used to set different levels of sensitivity of the autonomous household appliance. For example, the service unit can set the autonomous household appliance on increased alert for the time period of a planned medication intake, so that the autonomous household appliance increasingly searches the surroundings of the seating and lying furniture and other room areas associated with the medication intake for medication that has fallen off. The detection threshold of the autonomous household appliance can also be changed for time periods in which nursing events take place.

The auxiliary person unit can be designed for wireless opening of door locking units when a need for assistance would be detected. For this purpose, the auxiliary person unit can be made possible by suitable parameterisation in order to unlock radio door locks with the aid of a radio communication unit, thus enabling auxiliary persons to gain access to rooms otherwise closed from outside. This is helpful, for example, for sanitary rooms that are otherwise lockable from the inside.

The autonomous household appliance may also have a warning unit for emitting visual and/or audible warning signals when a person approaches the appliance by means of at least one environmental sensor. This reduces the risk of people in need of care accidentally stepping on the autonomous household appliance and falling. For example, the warning device may be set up in such a way that the closer the environmental sensors come to humans and animals, the clearer the visual and/or audible signal becomes.

The service unit is preferably integrated into a movable armrest or a movable shelf (e.g. table) of the seating or lying furniture. The armrest or shelf can be brought into a position by the seated user, for example by swivelling or bending it, in which the user can easily grasp the screen of the service unit integrated in the armrest or shelf and also operate it in the case of a touch-sensitive screen. The armrest thus provides both a support surface for the arms and a holder for the service unit, in particular for the monitor of the service unit, in order to bring the service unit, which is mounted on the monitor, into the user's face and control panel. This arrangement offers an advantage especially for visually impaired persons, as the positioning on the armrest is also optimal near vision and the eyes.

The integration of the service unit into an armrest or shelf, i.e. the integral installation into the armrest or shelf, has the advantage that the service unit is inconspicuous compared to the attachment to a stand decoupled from the armrest or shelf. A service unit mounted on a tripod can also be dismantled and installed more easily, whereas the service unit integrated in the armrest or shelf remains there in any case and is therefore reliably available. In this way, the technology required for personal monitoring and care is integrated into an existing (possibly mobile) piece of seating or reclining furniture and is reliably available at the centre of the person's life.

It is advantageous if the seating and lying furniture has a cup holder that is coupled with sensors for monitoring the patient's drink consumption from the container that can be positioned in the cup holder. This allows the service unit to be set up to output a reminder, for example via a loudspeaker, if the beverage intake is insufficient. The cup holder can have a thermal element to keep the cup or its contents warm and/or cool.

It is also advantageous if at least one microphone and/or loudspeaker is installed in the seating or lying furniture and connected to the service unit. The seating and reclining furniture can also have vital data sensors integrated in it.

The reliable administration of medication also plays a major role in the monitoring and care of people. It is therefore a task of the present invention to improve the drug administration of patients and to ensure the proper drug intake without influencing the normal daily routine.

The seating and lying furniture can be stationary. But it can also be mobile, i.e. moveable. This is the case if the seating or reclining furniture has castors that can be locked or lowered in order to be able to switch between a mobile mobile state and a safe stationary state.

This task is solved with the household appliance with the characteristics of claim 14. Advantageous forms of execution are described in the subclaims that depend on them.

It is proposed that the household appliance designed for the preparation of food with a receptacle has a dosing unit connected to the receptacle. The household appliance is intended and suitable for providing food for the user independently of the medication and is therefore fundamentally different from devices known from US 2016/0058245 A1, which are exclusively designed for the preparation of energy drinks with food supplements.

The dosing unit has a dosing vessel for the intake of medication. A control unit is provided for controlling the dosing unit, which is set up for the prescribed addition of medication from the dosing vessel to the food contained in the vessel depending on the preparation of a foodstuff.

A household appliance regularly used by the patient during the course of the day is used for the controlled administration of medication, whereby the medication to be administered is mixed with the normal preparation of the food, so that the medication can be dispensed automatically together with the food preparation and food intake, without the need for separate devices or devices for the allocation of medication. This combination of the dosage unit for the medication admixture with a household appliance is suitable for one-person households, as they are regularly found in nursing care for the elderly. The dosing unit can be attached to the household appliance as a separate part or integrated into the household appliance.

The household appliance preferably has a stirring unit in the container, which can then be used to mix the drug into the food at the same time.

The household appliance may have a heating and/or cooling unit coupled to the vessel. This allows the food to be prepared to be heated or cooled for cooking. With the aid of this heating and/or cooling unit, a suitable temperature can be set via the control unit for the dosing of food and in particular medication by means of suitable control. The dosing vessel may have several separate drug intake areas. The dosing unit is set up for the controlled mixing of selected drugs from the drug intake areas. This makes it possible to implement a more complex medication regulation in line with requirements, in which different drugs are prepared in the individual drug intake areas and mixed in line with requirements at the desired time or with suitable foods.

The dosing unit can have a grinding mechanism for comminuting drugs that are in solid form. In this way, tablets or capsules can be crushed and mixed into the food in such a way that they are prepared.

It is particularly advantageous if the drugs are already provided in doses of medication in packaging individually put together for the patient. This at least one package is then fed to the dosing unit, which, depending on the specified intake time for a medicine, opens an individual package or a packaging section provided for this purpose and doses it into a foodstuff. Such packaging can, for example, be a blister that provides individually packaged medicines in blister sections depending on the time of day. A blister strip can then be moved through the dosing unit with conveyor elements to bring a blister section, depending on the time of day, into the area of intervention of a dosing unit which opens the blister section and brings the liquid, viscous or solid content from the blister section into the vessel. For this purpose, the blister section can be flushed if necessary. It is also conceivable that a grinding unit is arranged between the blister section and the vessel in order to grind the medication before dosing.

It is also conceivable, however, that the medicines are provided in individual capsules depending on the time of day, which are then opened by the dosing unit for dosing the medicines contained therein. These separate capsules can also be arranged like a blister strip on a common carrier. Here, too, the drugs are stored individually and in portions in blister sections in a sterile manner and can be dosed by the dosing unit as required according to a medication schedule individually specified for the patient.

The dosing unit may be designed as an alternative or in addition to the dosing unit for introducing dosing liquid into the dosing vessel in order to dissolve the medicament to be dosed into the vessel, which is located in the dosing vessel, in the dosing liquid and/or to mix it with the dosing liquid, in order then to introduce this dosing liquid into the food in the vessel. In this way, a drug which is provided in liquid form in the dosage vessel can be rinsed out of the dosage vessel with the aid of the dosage liquid and mixed into the food with the dosage liquid. The dosing liquid itself can also be the food to be prepared in the container.

If water is used as the dosing liquid, this has the advantage that the dosing vessel is rinsed when dosing the document.

The dosing unit can be connected to a lid of the vessel or placed on the lid of the vessel. This makes it possible to use a standard household appliance, the lid of which is replaced by a lid fitted with a dosing vessel and dosing device. The dosing unit can at least partially be realized by an electronic control unit of the household appliance. However, it is also conceivable that, for example, a separate electronic dosing unit is installed in the lid of the device, which can be used to control the addition of medication as required. This can be time and event controlled. For example, sensors in the lid of the container can be used to detect that the household appliance is in operation. Depending on the time of day, a pre-programmed drug addition can then be started in this operating state.

It is advantageous if there is a data interface for importing prescription data that includes administration times, time intervals, quantities and/or contents of drugs to be administered. The control unit is then set up for dosing the medication depending on the prescription data read in via the data interface. Such a data interface can be used as a connecting plug to a data memory card (e.g. SD card), as a radio data transmission unit in the close range e.g. via WLAN or Bluetooth or in the far range via mobile radio communication, as a reading unit for a transponder (RFID) and/or as an optical data code reader (e.g. for UCR or barcode). With the aid of such a data interface, it is very easy to reliably transfer the recipe data from a recipe in electronic or paper form to the dosing unit of the household appliance. The easiest way to do this is to store the medication addition as an optically readable code in the prescription, whereby this prescription information only has to be transmitted to the household appliance via the data interface for mixing the medication and controlling the household appliance. This can reduce the influence of errors.

A blister pack or other medicine package can also be provided with coded information such as OCR codes, barcodes or RFID. The household appliance has a blister information read-out unit set up to read out this information in order to ensure that only the individual medication released for the household appliance is dosed into the food at dosage times appropriate to the time information possibly stored in connection with the blister sections. In addition, such information can be used as a control parameter for the after-treatment of the drug, for example by crushing.

In addition, an identity check and a comparison with the identity information on the blister pack is possible. Such a personal comparison can also be combined with an additional identity sensor on the household appliance. For example, the household appliance can have a fingerprint sensor to record the fingerprints of the person using the household appliance, so that the individual medication can only be administered if the released personal data matches. In this context, it is also conceivable to check the identity of a person in the vicinity of the household appliance by radio data comparison with a so-called Smart-Watch or an RFID transponder.

The provision and intake of medication can be simplified by the provision of medication in individually assembled blistered units. Single packs of different medicines in different pack sizes are avoided, which are often only partially used up.

The household appliance can be a kettle, an automatic cooking machine, a tea machine, a coffee machine, a kitchen machine, a bubbler or the like. This means that household appliances already available and used daily by the patient are used to ensure that a given medication is administered by admixture during food preparation, without the patient having to consciously take the medication at given times. This ensures that patients in need of care, and in particular dementia patients, can adhere to their medication plan without excessive care expenditure.

The drug admixture can be stored together with the information about the prepared food and can be retrieved as a data record for the nursing documentation. In this way it can be tracked which amount of fluid, which amount of energy, which amounts of fats, proteins and carbohydrates as well as vitamins and the like the patient has taken and at which times and intervals medication was added and then obviously taken.

It is advantageous if the household appliance is set up to receive current vital data of the person to be treated, for example from vital data sensors of the person (e.g. Smart-Watch). Such vital data can be for example blood pressure, pulse and pulse rhythm, oxygen saturation and body water content. The dosing unit can then be set up to regulate the administration of medication within a specified tolerance range depending on such received vital data.

The household appliance can have an alarm unit in order to send an alarm message, e.g. in the form of a nursing emergency call to a nursing service and/or to relatives, if food is not taken from the household appliance after preparation. In addition, the household appliance can be set up to log the administration of medication and, if necessary, transmit the patient's vital data to medical personnel online together with the vital data received from vital data sensors. It is also conceivable that the household appliance is set up to change the medication plan remotely via a data interface by the attending physician. Additional safety routines, such as certificate routines, should be implemented to ensure that interventions and changes in dosage can only be performed by authorized personnel.

The seating and reclining furniture with its service unit can form the central unit in which the other care aids, such as in particular the autonomous household appliance and the household appliance set up for administering medication, are brought together and networked. It forms a data bridge and central logistics unit for this purpose, so to speak, in order, for example, to control the medication intake with the help of the household appliance as a medicine alarm clock and to monitor the medication intake with the help of the mobile autonomous household appliance. The service unit of the seating or lying furniture can communicate with the household appliance in order to control the administration of medication or at least to retrieve information on medication admixture in foodstuffs, in order to monitor the correct intake of medication on this basis by actuating or querying the autonomous household appliance and/or further vital data sensors and, if necessary, to recognise a need for assistance in the event of deviations from specified environmental and/or vital data. The communication between the service unit of the seating or lying furniture and the autonomous household appliance enables demand-oriented monitoring of the person's surroundings in order to be able to follow the daily routine of the person to be looked after through the mobility of the autonomous household appliance and to monitor this inconspicuously with regard to any need for assistance. Vital data sensors can trigger further monitoring by the service unit and the care aids networked with it. Through the intercommunication of the nursing aids, valid information on the person's need for help can be derived that goes beyond the individual data of the autonomous household appliance or the household appliance. For example, sensitive data from the household appliance, which is set up to add medicines to food, can be used to trigger a monitoring trip through the autonomous household appliance in order to obtain further information on the need for help.

Further networking with other care aids is also conceivable, for example with vital data sensors of toilets, dishes, cutlery or the like, which are set up to detect the condition of the person to be cared for and/or with sensors on kitchen appliances, such as refrigerators (e.g. to determine the shelf life of food or its withdrawal), which also provide indicators of the need for help. The overall view of these indicators makes it possible, particularly with the help of the mobile autonomous household appliance, to verify the information on the need for help obtained from the summary of the data, to evaluate connections and to identify causes.

In this way, the autonomous household appliance can be controlled by the service unit in order to record environmental characteristics with adapted sensitivity, with which a need for help on the part of the person to be looked after can be recognised even more reliably and, if necessary, validated.

These routines may be implemented in conjunction with a computer program using program code means designed to evaluate environmental and, where appropriate, vital signs data and identify the need for assistance from such data when the computer program is run on a data processing unit.

The invention is explained in more detail below using an example. Show it.

Figure 1:
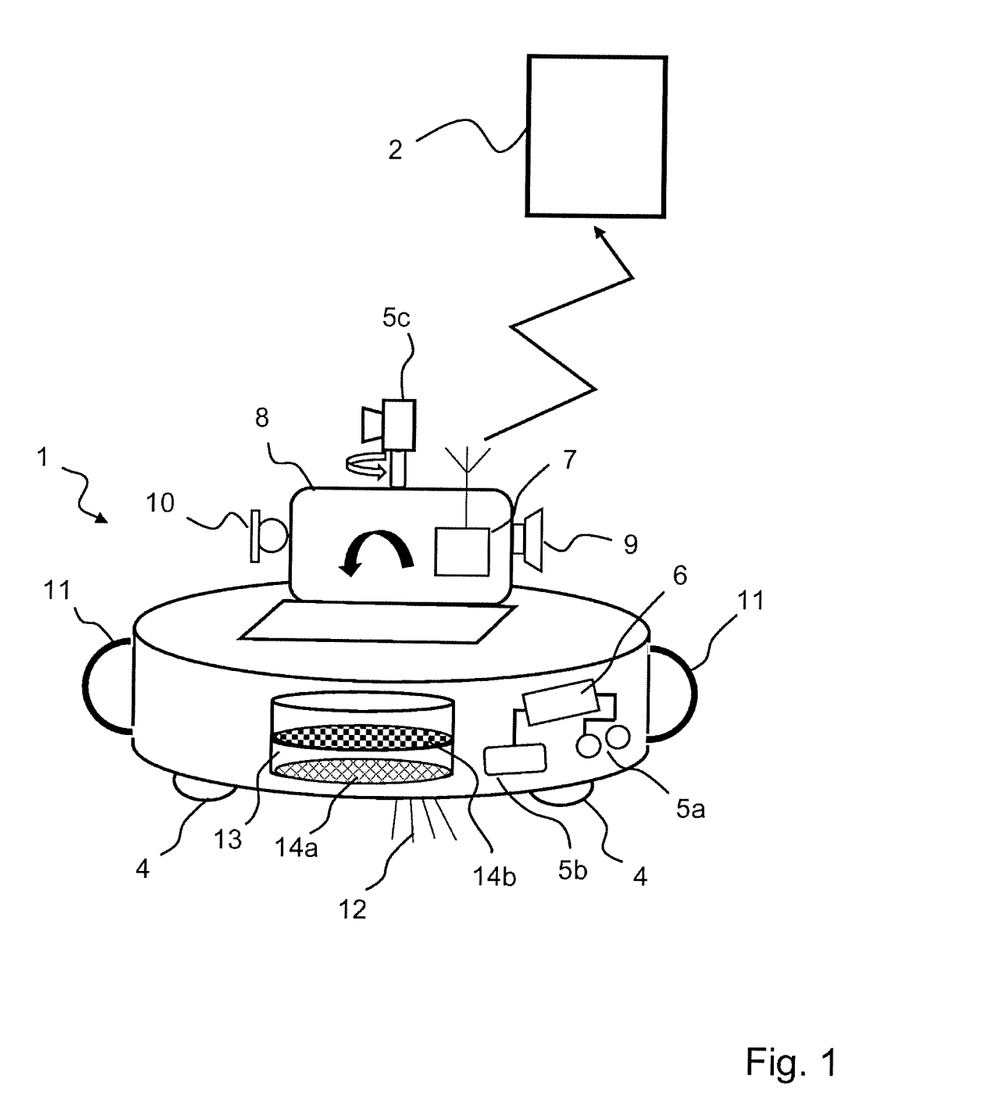
FIG. 1—Sketch of an autonomous household appliance with remotely located service unit.

FIG. 1 shows a sketch of an autonomous household appliance 1 with a remotely arranged service unit 2. The autonomous household appliance 1 is, for example, a suction robot with a platform 3 designed for autonomous movement. For this purpose the platform has 3 means of transport 4 e.g. in the form of wheels driven by electric motors as well as environmental sensors 5a, 5b for detecting obstacles. Such ambient sensors 5a can be e.g. ultrasonic distance sensors or tactile sensors 5b with sensors that can be moved when an obstacle is touched, optical sensors such as reflection light barriers, magnetic field sensors or similar. It is also conceivable that platform 3 has a positioning unit for determining the position of platform 3, such as a satellite navigation receiver or an in-house positioning system.

These environmental sensors 5a, 5b are connected to a control unit 6, which in turn is equipped to control the means of transport 4 depending on detected obstacles or distances.

Such an autonomous household appliance 1 has now been further developed in such a way that it is set up to detect the need for help of a person depending on the environmental characteristics detected by the environmental sensors 5a, 5b, 5c. For this purpose, the autonomous household appliance 1 preferably still has a camera 5c as an ambient sensor for taking pictures of the surroundings. This camera 5c can be permanently connected to platform 3. However, it is advantageous if the camera 5c can be swivelled and/or rotated as indicated by the arrow. Alternatively, a 380° camera can be used to observe the entire spatial angle range of the surroundings of platform 3.

The autonomous household appliance 1 also has a communication unit 7, which has a wireless communication link with the remotely located service unit 2 for establishing a wireless communication link.

The evaluation of the data of the environmental sensors for the recognition of a need of assistance of a person can be carried out by a computing unit of the autonomous household appliance 1. For example, the control unit 6 can be suitably programmed or an additional auxiliary person unit 8 can be connected to platform 3 as an additional module. However, it is also conceivable that the evaluation of the data of the environmental sensors 5a, 5b, 5c after wireless transmission takes place centrally in the remote service unit 2, which is then set up to recognise the need for help of a person depending on the environmental characteristics, e.g. by suitable programming.

The autonomous household appliance 1 can also have at least one loudspeaker 9 and at least one microphone 10 to establish a voice communication connection to the person to be looked after. This voice communication connection can then be established wirelessly via the communication unit 7 with the remotely located service unit 2.

The activation of the person assistance unit 8 and in particular of the camera 5c and the microphone 10 can take place time-controlled in defined monitoring intervals or at specified monitoring times. It is also conceivable, however, that the person assistance unit 8 is activated remotely via the service unit 2 if care personnel without visiting the person to be cared for would like to determine whether the person to be cared for is in need of assistance.

The autonomous household appliance 1 can also have handle elements 11, which are coupled with a vital data measuring unit integrated e.g. in the control unit 6 or the personal auxiliary unit 8. If a person touches these handle elements, for example, electrical impedance measurements can be used to determine the water and fat content. However, it is also possible to integrate an optical finger pulse unit for measuring pulse and oxygen saturation values. This is achieved by reflection measurement in two wavelength ranges (red and infrared light) by means of commercially available reflection light barriers trained for this purpose, which can be easily integrated into the handle elements 11.

The autonomous household appliance 1 also has a floor cleaning unit, e.g. with rotating bristles 12 or cloth.

It is now conceivable that this part of the floor cleaning unit also has integrated environmental sensors. For example, sensors can be integrated into the bristles 12 or cloths. It is conceivable that in the platform a unit for moistening the bristles has 12 or lobes with a detection liquid for certain substances to be detected, such as alcohol, urine, blood or the like. It can then be photodiodes or phototransistors in certain wavelength ranges or a colour camera by means of optical sensors. This makes it easy to check whether the substance to be monitored has been found in the vicinity of the autonomous household appliance 1 by changing the detection liquid and changing its colour.

It is also conceivable, however, that electronic sensors are integrated into the bristles 12 or cloth, whereby wiring to the control unit 6 or the auxiliary person unit 8 is then carried out or these environmental sensors are read out wirelessly, e.g. by means of UWB.

If platform 3 is designed as a suction robot, it is recommended that a preferably transparent collection container 13 is provided to collect particles extracted from the floor. The collection container 13 then has a coarse filter 14a to allow larger particles such as tablets in particular to pass through, and a downstream fine filter 14b. The tablets relevant for the identification of a potential need for help, which the person to be looked after did not take properly but lost on the ground, then collect in the collecting container 13 and are available there for the identification of the need for help. For this purpose, an optical sensor or a camera, for example, can be coupled to the collection container 13 in order to detect the presence of tablets and the like.

Other environmental sensors, such as alcohol detectors, urine detectors and the like, can also be installed in the collection container 13 in order to detect characteristic properties for a need for assistance on the basis of the absorbed substances.

Figure 2:
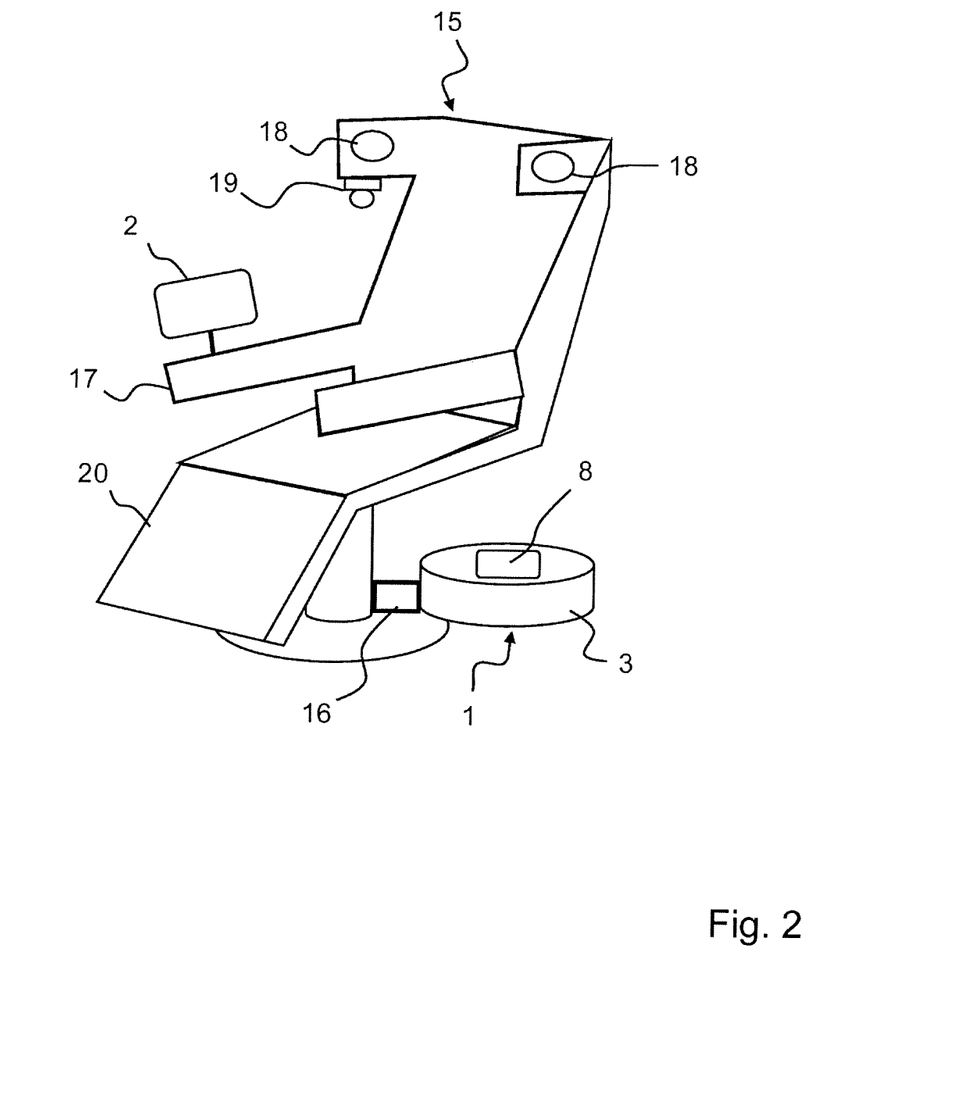
FIG. 2—Sketch of a piece of seating furniture with integrated service unit and charging station for an autonomous household appliance.

FIG. 2 shows a seat 15 for a person to be cared for. This can be a comfortable wing chair, but also a nursing bed or something similar. The seating furniture 15 now has a charging station 16 in its foot area, to which the autonomous household appliance 1 can dock in order to recharge its energy stores. This can be caused, for example, by electric charging of accumulators of the autonomous household appliance 1. However, the transfer of solid or liquid fuels is also conceivable.

As the charging station 16 is located in the foot area of the seat furniture 15, the autonomous household appliance 1 is parked in a less conspicuous position, which forms the usual centre of life for the person to be looked after. This shortens the distances to the priority areas for monitoring the need for assistance. The monitoring frequency for this room area is increased, as the autonomous household appliance 1 can regularly check the surroundings of the seating furniture 15 due to the spatial proximity. In this area, however, the person to be looked after regularly takes the medication and lost medication in the vicinity of the seating furniture can be recognised that there is a danger of inadequate medication intake and thus a need for help. Medicines on the floor can be detected, for example, by the collection container 13 for tablets or similar and by alcohol sensors for liquid medicines.

The seat furniture 15 is also designed as a command centre for the person to be looked after and has a swivel, sliding and/or telescopic service unit 2 arranged on the seat furniture 15. This service unit 2 can, for example, be a tablet computer with a monitor and an input unit. This service unit 2 can, for example, be arranged on a swivelling armrest which can be folded down or moved so that service unit 2 can be easily operated by the person sitting on the seating furniture.

In addition, loudspeakers 18 and a microphone 19 can be integrated into the seating furniture 15. In this way, handsfree talking can be established via a communication link with caregivers who are not in the room.

For convenience, a foldable footrest 20 may be provided which covers and protects the charging station 16 and the autonomous household appliance 1 inside it.

Service unit 2 can also be set up to control the lighting in the apartment of the person to be looked after. Service unit 2 preferentially works in conjunction with autonomous household appliance 1, which detects movement of the person to be cared for by means of motion sensors and then controls the light depending on the lighting conditions detected by light sensors or the time of day in order to guide the person to be cared for safely through the home. It is advantageous if the autonomous household appliance 1 is activated during a movement of the person and if necessary guides the person through the process of approaching the vehicle and through light signals. The autonomous household appliance 1, for example, can be suitably programmed to be parked on the nursing bed at night and, if the person to be cared for gets up, to switch on the light in the room automatically and remotely and, if detected, to use light signals to guide the person to be cared for to the washrooms, for example, and then to return to the nursing bed in this night situation.

For example, the autonomous household appliance 1 can be programmed in such a way that it always leads to the washrooms between 6 a.m. and 8 a.m. with the lighting function and then to the kitchen, as the patient takes his medication there. This recorded routine can later be (re-) activated via the system, so that the system can automatically trigger the execution (e.g. by means of a signal or wake-up function) if the person forgets such routine treatments in a creeping process, e.g. due to dementia. The autonomous household appliance 1 is thus set up for activity and inactivity detection with a reminder function.

This can be achieved relatively easily by situation-dependent programming of care routines for an autonomous household appliance 1, as the autonomous household appliance 1 has a self-propelled platform 3 anyway.

Autonomous household appliance 1 can also be set up to drive through the surroundings at specified intervals and to check whether the person to be cared for is in a state in need of assistance. In this case, monitoring trips can also be specified at times of risk. Such risk periods can be time periods in which medication is intended. For example, a household appliance designed to add medication to food may be linked to the autonomous household appliance in order to trigger a monitoring drive of the autonomous household appliance in the room of the other household appliance in connection with the addition of medication to food and to monitor whether food with the medication has fallen to the floor or been spilled or correctly consumed.

By a daily recording and logging of the activities by the autonomous household appliance 1 a logic can be stored, so that deviations from the routine (e.g. the daily routine of the person to be cared for) can be indicators for the fact that a situation exists in the support need is given and thus a help call function—as "memory function"—is acti-activated.

For this monitoring, the monitoring sensors intended for this purpose and which may interfere with privacy, such as the camera 5c and the microphone 10, are then activated. This can be done by unfolding the person assistance unit 8.

It is also advantageous if not only the autonomous household appliance 1, but also or alternatively the seating or lying furniture has 15 handles for measuring vital data, in particular cardiovascular data of the person to be cared for. Such vital data sensors can therefore also be easily integrated into the seating or reclining furniture and connected to service unit 2.

It is conceivable that the autonomous household appliance 1 is set up to perform a specified background function after triggering a help or emergency call function and establishing a communication connection. For example, the playback of pre-programmed or preset videos or music can be triggered as soon as a call for help has been activated in order to defuse stress situations for the person to be cared for. Many people panic when they fall, for example. The waiting time then appears endless and can cause additional stress. Since humor and music relax and create a distraction from the acute event, the background function makes it possible to mentally shorten the waiting time and reduce further stress situations.

As a technical assistance system, however, other objects can also be used that are normally used by people in their daily lives.

For example, it is conceivable to equip a helmet or hat with sensors for fall detection. Here, too, at least one sensor for fall detection is integrated into this headgear. This can be an acceleration sensor, a magnetic field sensor, a height sensor, a pressure sensor or a combination of such sensors. A radio data transmission unit and a control unit are also integrated into the headgear. Here, too, a location sensor for position detection, a charging function, a microphone, a camera, but also heat sensors can be integrated.

If a fall of the person wearing the headgear or a need for help is detected by these sensors, an emergency and help call function can be activated automatically. It is also conceivable that the emergency and help call functions are activated by voice commands. The radio data transmission unit can be used to establish voice and, if necessary, image communication with the person in such an emergency or emergency. The location data, a photo or video and vital data can then be transmitted via the technical assistance system to an emergency call centre or to predetermined relatives.

If the person no longer communicates completely, the help system is automatically activated and an automatic image transmission to the specified person can take place.

The sensors integrated into the headgear can be used to determine, for example, whether the vital values are within the specified range. In this way, for example, dizziness or fatigue can be detected.

The headgear control unit can also be used to control automatic regulation of ventilation in the event of excessive heat, supply air reduction and, if necessary, heat supply in the event of excessive cold, wind influence and rain protection. The sensors can also be used to measure the weather conditions (temperature, heat, water/precipitation or snow, etc.). Such a headgear can be used for example for riding, skiing, motorcycling, paragliding, water sports, e-biking etc. by people who do not require care. When activated, the sensors are used to check whether the headgear is falling on the ground or whether a defined fall speed is being measured in order to switch to an emergency call mode in standby mode.

This monitoring function can be activated, for example, by means of a chin strap equipped with a switch. When the chin strap is closed, the circuit is closed and the monitoring function is activated.

Figure 3:
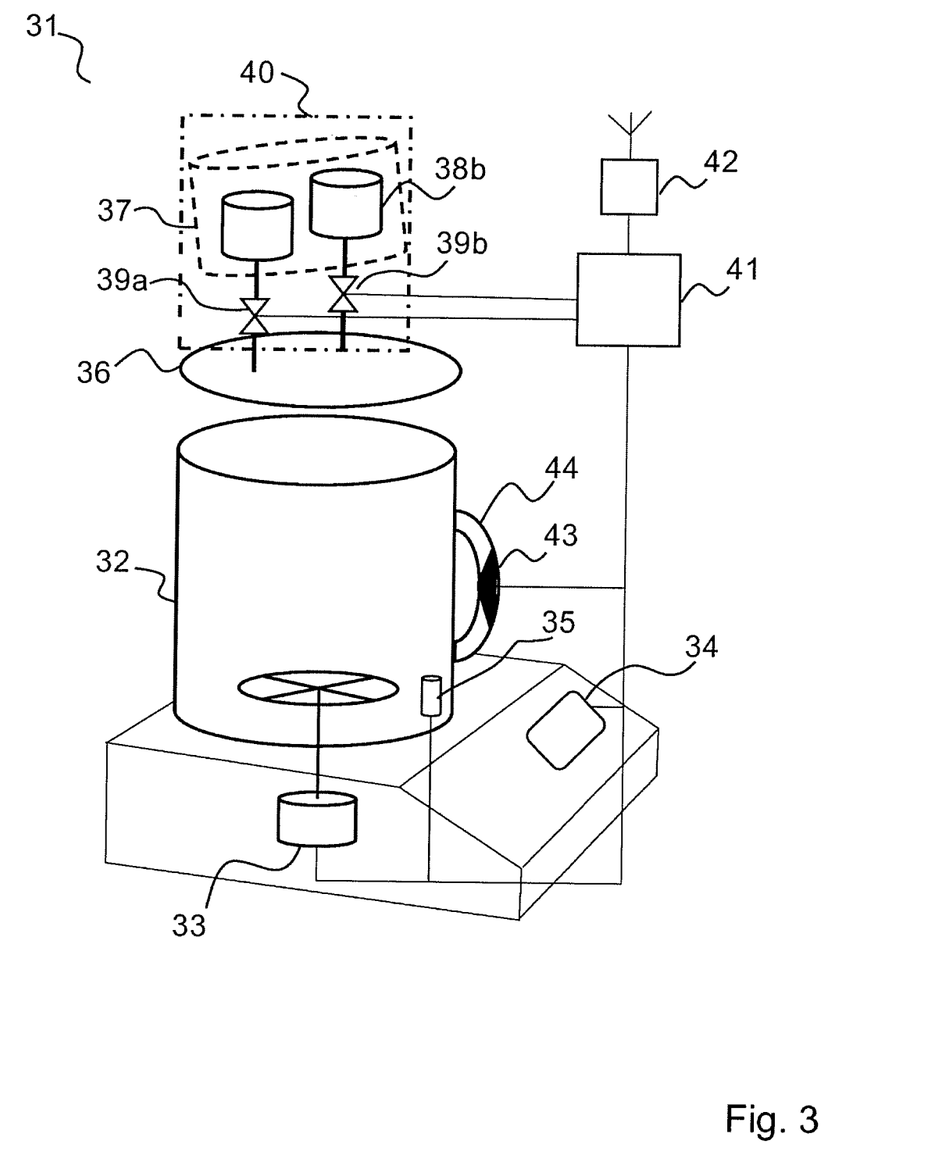
FIG. 3—Drawing of a household appliance with dosing unit for the admixture of medicines.

FIG. 3 shows a sketch of a household appliance 31 designed to prepare food. For this purpose, the household appliance 31 has at least one receptacle 32 with a stirring unit 33 intended for mixing the foodstuffs contained in the receptacle 32. Household appliance 31 in the example is a kitchen appliance in which 34 recipes are selected via a control unit and the step-by-step preparation of food is carried out by dosing and stirring with the stirring unit 33 and, if necessary, heating and cooling with a heating and/or cooling unit 35. The vessel 32 has a lid 36 which can be placed on the vessel 32.

In the example shown, the lid 36 is connected to a dosing vessel 37. For example, the dosing vessel 37 can be permanently connected to the lid 36 and/or coupled to the lid 36 via a hose system and thus to the vessel 32 in the attached state. The dosing vessel 37 can have several drug intake areas 38*a*, 38*b*, each of which can be connected via a dosing valve 39*a*, 39*b* with an opening in the lid 36 and thus with the vessel 32. The dosing valves 39*a*, 39*b* are part of the dosing unit 40 in order to dose drugs in solid or liquid form into the vessel 32 as required, which are prepared for admixture in the dosing vessel 37. A control unit 41 is provided for this purpose, which controls the medicines with the dosing valves 39*a*, 39*b* or dosing flaps or the like, to add the medicines according to predetermined rules in a time and quantity controlled manner during the preparation of the food in the container 32.

The program for dosing the medication can be fed to the control unit 41 via the input unit 34 or via another data interface. Such a data interface can be, for example, a slot with plug connectors for receiving and contacting a data memory card (SD card or similar), a radio data transmission unit 42 for radio data communication, an RFID reader for reading data from a radio transponder or an optical sensor for reading recipe data, for example via a barcode or OCR code or similar.

In the example shown, the radio data transmission unit 42 is set up together with the control unit 41 to also send an alarm message to a remote care emergency call centre or a relative if it is detected that the automatically prepared food has not been removed at specified times. The removal of the food can be sensed by detecting the removal of the container 32 from the platform of the household appliance 31 or at least the removal of the lid 36, e.g. by means of a button.

Furthermore, the household appliance 31 may have at least one sensor 43 for recording vital data of the person operating the household appliance 31. For example, a vital data sensor 43 can be arranged on the handle 44 of the vessel 32 in order, for example, to optically record the pulse rate and, if necessary, the oxygen saturation of the patient with a finger pulse sensor and/or other vital data, such as water content or similar, with an impedance measurement when gripping the vessel 32 on the handle 44.

The control unit 41 can also be set up by suitable programming, for example, to adjust the medication administration depending on the vital data supplied to the control unit 41. This vital data can, for example, be transmitted via the radio data transmission unit 42 from other vital data sensors to the household appliance 31. Such vital data sensors can be, for example, a personal scale, a fitness wristband of the patient and the like, which communicate wirelessly with the household appliance, for example with the Bluetooth or WLAN communication standard.

Vital data monitoring is very useful for maintenance. This reduces the amount of personal care required and enables an independent daily routine.

It is therefore advantageous if technical assistance systems are integrated into existing emergency call systems.

For example, many elderly people use a rollator to reduce the risk of falling. It is helpful if such devices as a rollator, a wheelchair, an e-bike or similar vital data sensors, a data transmission unit, a location sensor, a light control, a charging function, a microphone and a camera are also available. With the help of the vital data sensor, a fall can be detected and a call for help sent to a home emergency call centre via the radio data transmission unit. The emergency and help call function can, for example, also be activated via the microphone using voice commands. An emergency or help call can also be triggered automatically if certain predefined indicator characteristics have been recognized. With the help of the radio data transmission unit and the microphone, a loudspeaker and the camera, voice and visual communication can be established from the emergency call centre to the person. For example, a mobile phone function can be integrated into the auxiliary device.

Vital data sensors monitor vital values such as dizziness or fatigue. For this purpose, optical sensors and/or impedance sensors can be installed on the handles to detect pulse data, oxygen saturation values and other cardiovascular information of the patient.

The device is then set up to activate the emergency call system by mechanical movements and contact with the handles through the hands of the user. For example, if a rollator falls to the ground in this activation mode, hits an object or falls into an excessive angle of inclination, and then hands lose contact with the rollator, this "standby status" activates an emergency call and emergency mode. In this emergency mode, the first step is to establish communication via a radio data channel with a nearby mobile phone or with a remote emergency call centre.

The auxiliary device may have an accumulator for supplying electrical energy. The kinetic energy of the aid is used, for example, by generators integrated into the wheel hub to recharge the batteries during use. However, it is also conceivable that other elements such as solar cells are used to generate electrical energy in order to provide the energy required to charge the batteries.

Such an aid can then be combined with the household appliance 31 to ensure that the household appliance 31 can be controlled as required, for example with the aid of the radio data transmission unit 42.

Figure 4:
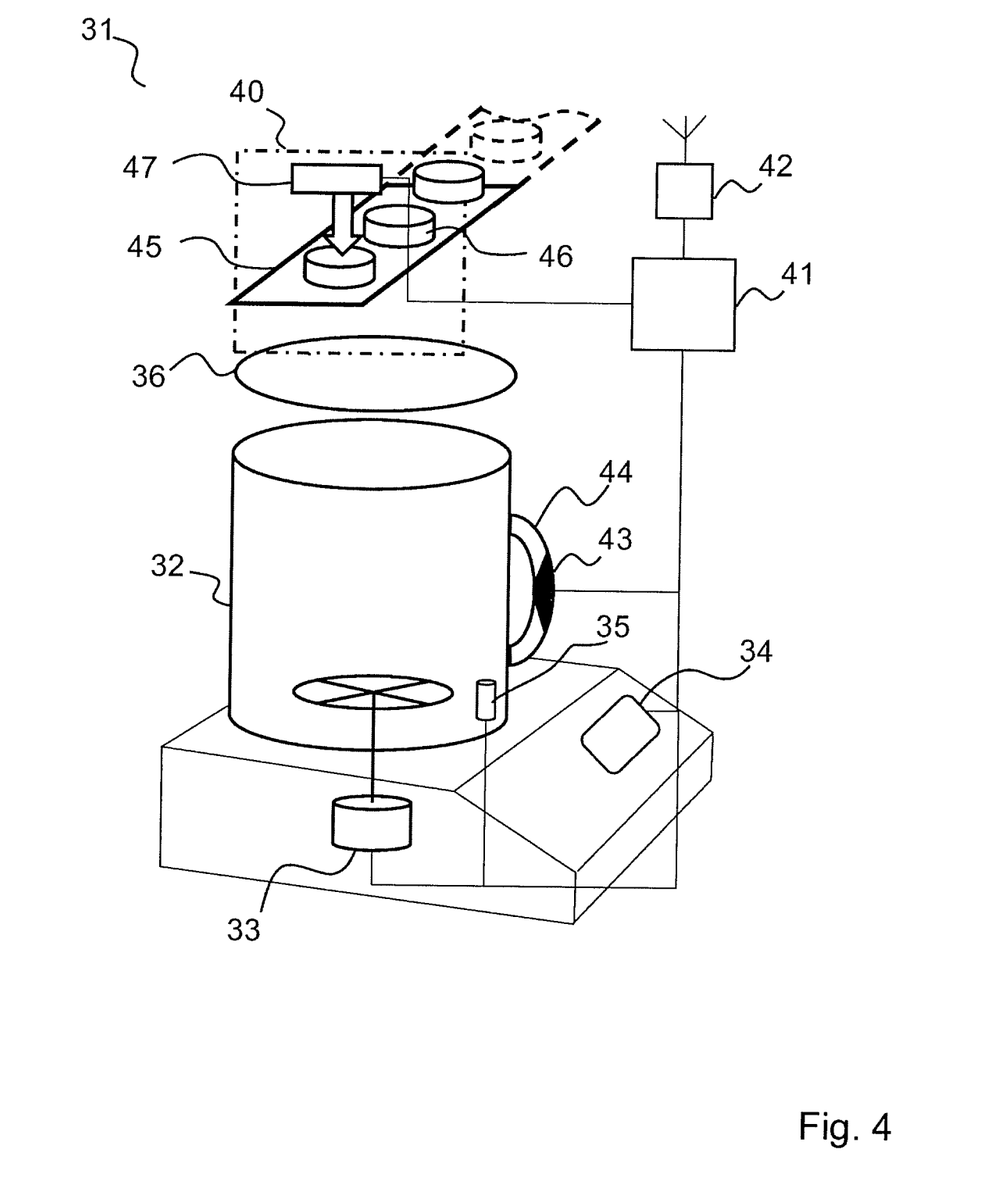
FIG. 4—Drawing of the household appliance from FIG. 3 with dosing unit set up for mixing medications from blister packs.

FIG. 4 shows a sketch of the household appliance 31 from FIG. 3 with the dosing unit 40 set up for the admixture of medicines from blister packs. The medicines are already provided in doses of medicines in packaging individually put together for the patient. This blister package 45 is then fed to the dosing unit 40, which opens a correspondingly prepared blister section 46 and doses it into a foodstuff, depending on the specified intake time for a medicine. The blister package 45 (e.g. blister strips) is moved by the dosing unit 40 with conveyor elements to bring a blister section 46 into the engagement area of a blister opening unit 47, which opens the blister section 46 to bring the liquid, viscous or solid contents from the blister section 46 into the vessel 32, depending on the time of day. The blister section 46 can simply be opened mechanically, whereby the drug falls from the blister section 46 by gravity into the vessel 32. The medication can also be transported out of blister section 46 with a plunger. It is also conceivable that the blister section 46 is flushed to remove the drug and introduce it into vessel 32. A grinding unit can be placed between blister section 46 and vessel 32 to grind the medication as required before dosing.

Instead of the shown blister packaging 46 in the form of blister strips, individual capsules can also be provided. Depending on the time of day, the capsules are then opened by the dosing unit 40 to dose the medication they contain. For improved handling, these separate capsules can also be arranged like a blister strip on a common carrier. Here, too, the drugs are stored individually and portioned in a different type of blister packaging 45 in a sterile manner and can be dosed by the dosing unit 40 as required according to a medication schedule individually specified for the patient.

The Dosing Unit 40 may have a cooling unit to properly store the medication provided in the blister packs 45 at a temperature that may be required.

The blister packaging 45 only has to be inserted into the dosing unit 40 by nursing staff during longer periods of time, which then automatically and reliably provides it to the patient in accordance with a prescribed medication plan. A time-consuming and error-prone manual compilation and provision of drugs is no longer necessary. This allows a considerable reduction in the amount of care required and makes care safer without the need for intermediary medical personnel.

Figure 5:
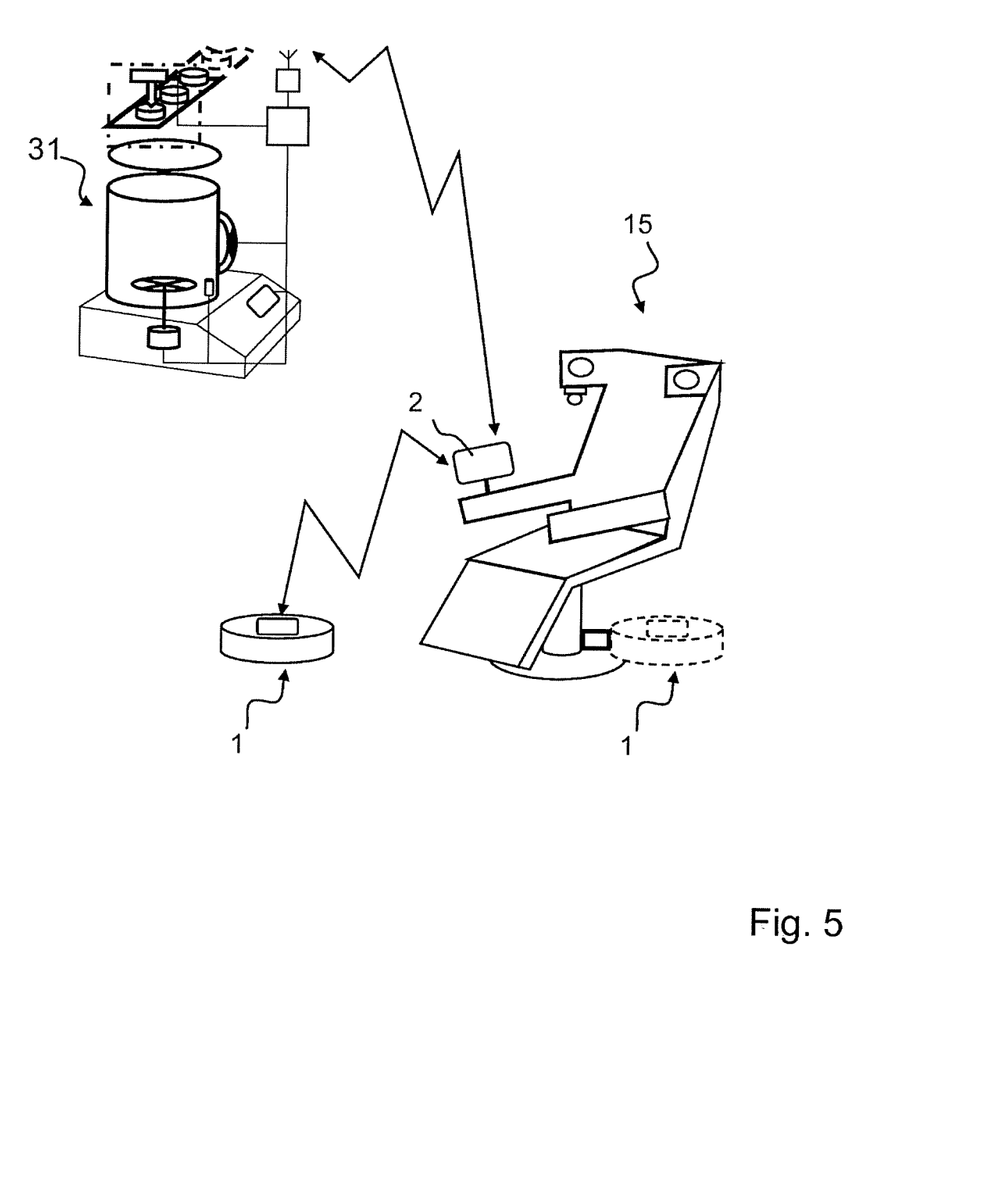
FIG. 5—Sketch of the system consisting of seating furniture, autonomous household appliance and household appliance for food supply with medication added.

FIG. 5 shows a sketch of the system consisting of seating furniture 15, autonomous household appliance 1 and household appliance 31 for the supply of food under medication admixture. As the centre of life, seat 15 and its service unit 2 form a central unit in which the other care aids, such as in particular the autonomous household appliance 1 and the household appliance 31 set up for administering medication, are brought together and networked. It forms a data bridge and central logistics unit for this purpose, so to speak, in order, for example, to control the medication intake with the help of the household appliance 31 as a medication alarm clock and to monitor the medication intake with the help of the mobile autonomous household appliance 1. The service unit 2 of the seating furniture 15 can communicate with the household appliance 31 in order to control the administration of medication or at least to retrieve information on medication admixture in foodstuffs, in order to monitor the correct medication intake on this basis by actuating or querying the autonomous household appliance 1 and/or further vital data sensors and, if necessary, to recognise a need for assistance in the event of deviations from predetermined environmental and/or vital data. The communication between the service unit 2 of the seating furniture 15 and the autonomous household appliance 1 enables demand-oriented monitoring of the person's surroundings in order to be able to follow the daily routine of the person to be looked after through the mobility of the autonomous household appliance 1 and to monitor this inconspicuously with regard to any need for assistance.

The invention claimed is:

1. An autonomous domestic appliance, comprising:
    a platform having
        locomotion means,
        one or more environment sensors for detecting characteristics of an environment, and
        a control unit,
        wherein the one or more environment sensors are connected to the control unit and the control unit is set up for autonomous movement of the domestic appliance by actuation of the locomotion means as a function of detected environmental characteristics by the one or more environment sensors, and for constant departure of an area in order to carry out an actual domestic activity; and
    a communication unit for establishing a communication connection with a remotely located service unit,
    wherein the autonomous household appliance is set up to recognize a need for help of a person as a function of the detected environmental characteristics,
    wherein at least one environment sensor of the one or more environment sensors detects one or more properties of elements collectable from the environment.

2. The autonomous domestic appliance according to claim 1, further comprising a person assistance unit integrated into the autonomous domestic appliance which performs the recognition of the need for help by a person as a function of the detected environmental characteristics, and wherein the person assistance unit is set up to wirelessly transmit a request for assistance via the communication unit in the event of a recognised need for assistance.

3. The autonomous domestic appliance (1) according to claim 1, wherein the service unit is a component of the domestic appliance and is designed as a person assistance unit set up to recognise the need for assistance of a person as a function of the environment characteristics, wherein the person assistance unit determined the need for assistance of a person based on transmissions received via the communication unit.

4. The autonomous domestic appliance according to claim 1, further comprising:
- at least one microphone for detecting sound signals; and the auxiliary
- a person assistance unit configured for command-controlled movement towards a sound source detected by said at least one microphone, and/or
- for recognizing the need for assistance as a function of a comparison of detected sound signals with predefined sound patterns.

5. The autonomous household appliance according to claim 1, wherein the autonomous household appliance is configured as a floor cleaning robot, and further comprising a collecting container with a coarse filter unit (14a) which is connected to the floor cleaning unit and is suitable for collecting medicines lying on a floor.

6. Autonomous household appliance according to claim 1 further comprising a person assistance unit which performs the recognition of the need for help by a person as a function of the detected environmental characteristics, and wherein the person assistance unit is set up for activating at least one camera and one microphone, if a need for assistance has been detected by of at least one scanning sensor, gas sensor, light sensor and/or sound level sensor.

7. The autonomous household appliance according to claim 1 wherein at least one of the environment sensors is adapted to detect blood, urine, alcohol or vomit.

8. The autonomous household appliance according to claim 1 wherein at least one of the environment sensors is set up to determine room air parameters, and further comprising a auxiliary person assistance unit which performs the recognition of the need for help by a person as a function of the detected environmental characteristics and which is set up to detect a need for assistance when a detected oxygen concentration falls below a predefined level and/or when urine content is detected.

9. The autonomous domestic appliance according to claim 1 wherein at least one environment sensor of the one or more environment sensors is integrated in bristles or cloths of a floor cleaning unit.

10. The autonomous domestic appliance according to claim 1 further comprising at least one interface for connection of one or more personal vital data sensors, and is set up for evaluation and/or transmission of sensor data detected with the one or more personal vital data sensors via the communication unit to a remote service unit.

11. Seating or lying furniture with a service unit arranged pivotably, displaceably and/or telescopically on the seating or lying furniture, wherein the service unit has a monitor and an input unit and is set up for communication with the autonomous household appliance of claim 1, and comprising a charging station for docking and charging the autonomous household appliance with energy arranged in a foot region of the seating or lying furniture.

12. The seating or lying furniture according to claim 11, wherein the service unit is integrated into a movable armrest or a movable shelf of the seating or lying furniture.

13. The seating or lying furniture according to claim 11 further comprising at least one microphone and/or loudspeaker built into the seating or lying furniture, wherein the at least one microphone is connected to the service unit.

14. A household appliance for preparing foodstuffs, comprising: having
- a vessel;
- a metering unit is connected to the vessel, wherein the metering unit has a metering vessel for receiving medicaments; and
- a control unit for controlling the metering unit, wherein the control unit is set up for predetermined admixing of medicaments from the metering vessel with foodstuff located in the vessel as a function of the preparation of a foodstuff.

15. The household appliance according to claim 14, wherein the metering vessel has a plurality of drug-receiving regions which are separated from one another, and wherein the metering unit is set up for controlled admixture of selected drugs from one or more of the drug-receiving regions.

16. The household appliance according to claim 14 further comprising a dosing unit designed for receiving blister packs and for dosing medicaments packaged in the blister packs individually for patients and depending on the time of day by opening a blister pack and removing and introducing one or more medicaments contained therein into the vessel.

17. The household appliance according to claim 14 wherein the vessel is selected from the group consisting of an electric kettle, an automatic cooking machine, an automatic tea machine, an automatic coffee machine, an automatic kitchen appliance, and a water sprinkler.

18. The autonomous domestic appliance of claim 1 configured as a lawn mowing robot.

19. The autonomous domestic appliance of claim 1 configured as a floor cleaning robot.

* * * * *